(12) United States Patent
Xian et al.

(10) Patent No.: US 9,494,592 B2
(45) Date of Patent: Nov. 15, 2016

(54) REACTION-BASED FLUORESCENT PROBES FOR SULFANE SULFUR AND THE APPLICATION IN BIOIMAGING

(71) Applicant: Washington State University, Pullman, WA (US)

(72) Inventors: Ming Xian, Pullman, WA (US); Wei Chen, Pullman, WA (US)

(73) Assignee: Washington State University, Pullman, WA (US)

( * ) Notice: Subject to any disclaimer, the term of this patent is extended or adjusted under 35 U.S.C. 154(b) by 45 days.

(21) Appl. No.: 14/250,481

(22) Filed: Apr. 11, 2014

(65) Prior Publication Data

US 2014/0308696 A1 Oct. 16, 2014

Related U.S. Application Data

(60) Provisional application No. 61/811,913, filed on Apr. 15, 2013.

(51) Int. Cl.

| | |
|---|---|
| A61B 5/00 | (2006.01) |
| A61B 8/00 | (2006.01) |
| A61B 10/00 | (2006.01) |
| G01N 33/58 | (2006.01) |
| C07D 493/10 | (2006.01) |
| C07D 311/16 | (2006.01) |
| A61K 49/00 | (2006.01) |

(52) U.S. Cl.
CPC ........... *G01N 33/582* (2013.01); *C07D 311/16* (2013.01); *C07D 493/10* (2013.01); *A61K 49/0041* (2013.01); *A61K 49/0043* (2013.01); *Y10T 436/182* (2015.01)

(58) Field of Classification Search
CPC ...................... A61K 49/0043; A61K 49/0041
See application file for complete search history.

(56) References Cited

U.S. PATENT DOCUMENTS 6,162,931 A * 12/2000 Gee ........................ C07C 37/055
430/345

OTHER PUBLICATIONS

Bieniarz et al. (Bioconj. Chem. 1994, 5, 31-39).*

* cited by examiner

*Primary Examiner* — Michael G Hartley
*Assistant Examiner* — Melissa Perreira
(74) *Attorney, Agent, or Firm* — Whitham, Curtis & Cook, P.C.

(57) ABSTRACT

Reaction-based fluorescent probes are provided which detect, for example, biologically important sulfane sulfur species (persulfide, polysulfide, and elemental sulfur) in, for example, complex and living systems. The probes are high in selectivity and sensitivity to sulfane sulfurs. Moreover, probes are suitable for bioimaging sulfane sulfurs in living cells.

7 Claims, 9 Drawing Sheets

FIGURE 3A
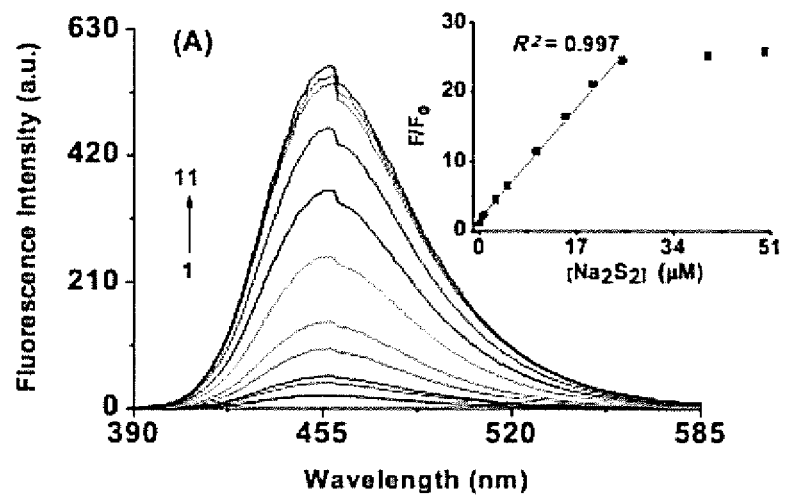
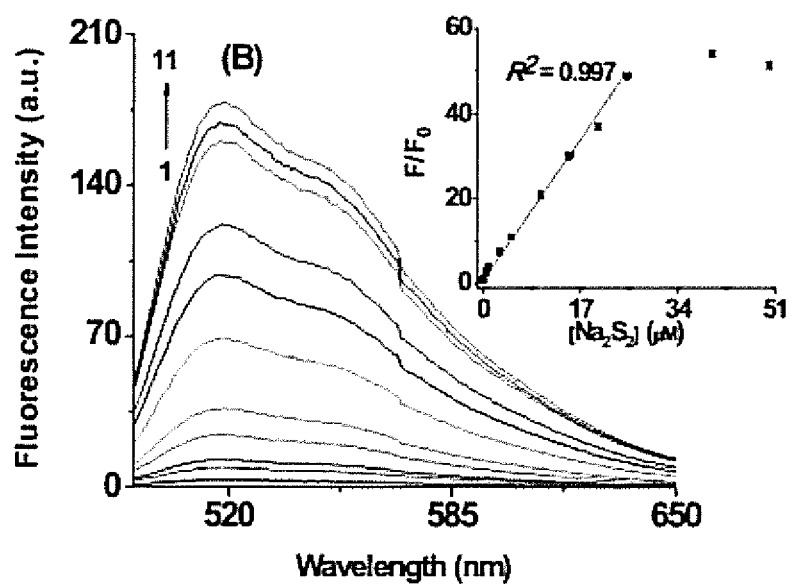
FIGURE 3B

FIGURE 4A
FIGURE 4B
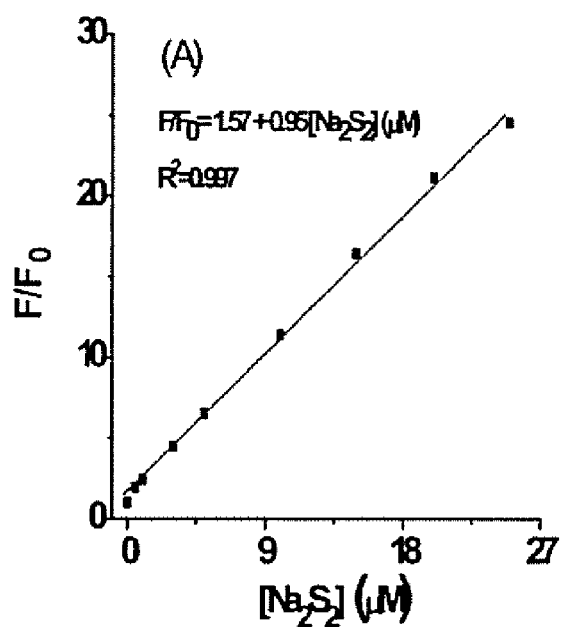
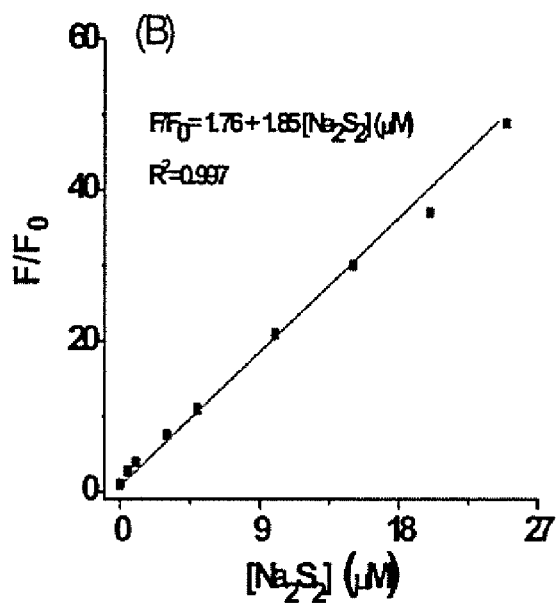

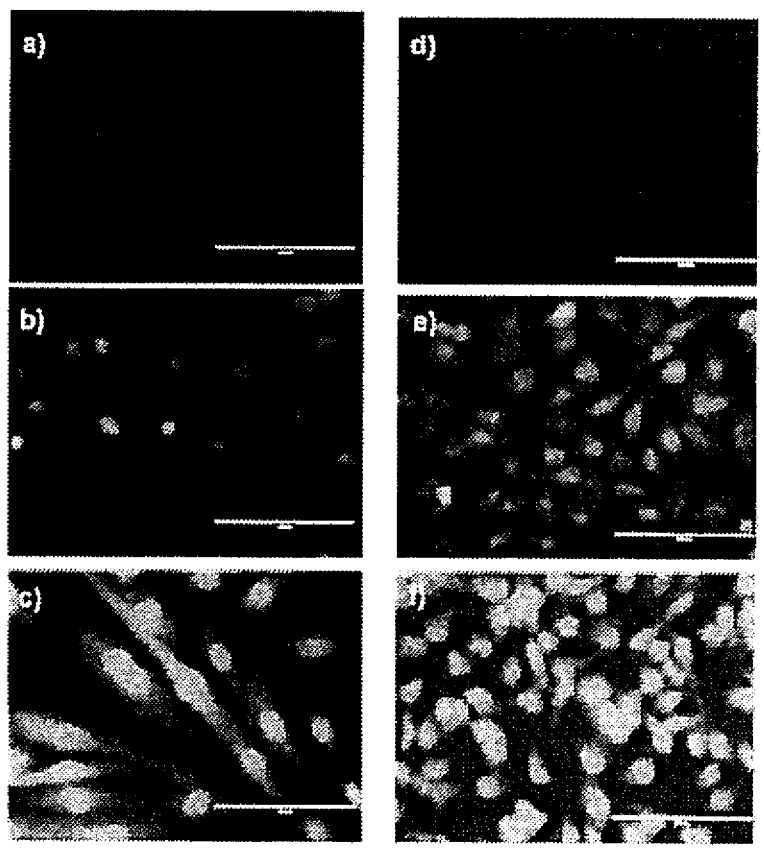
FIGURES 6A-F

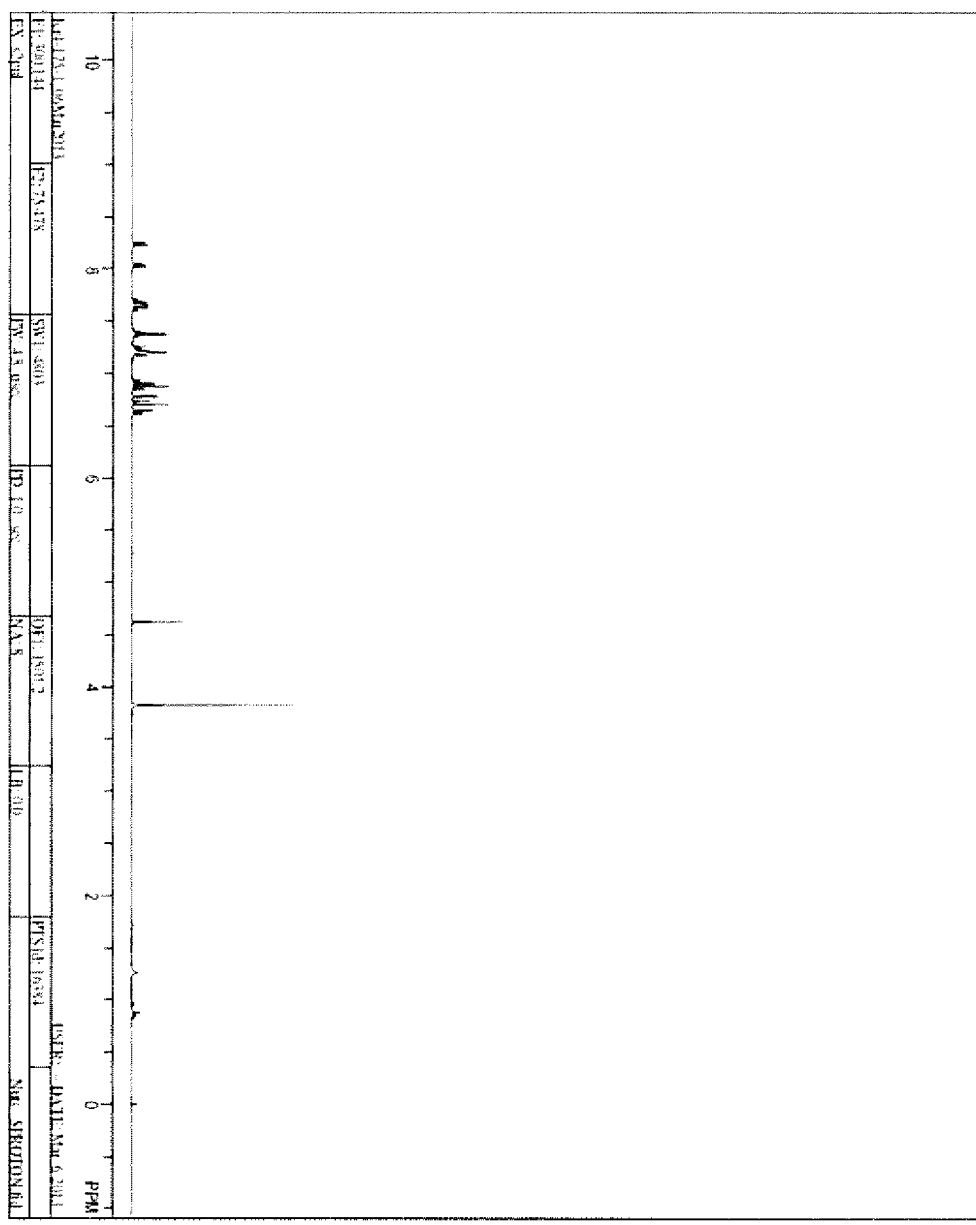
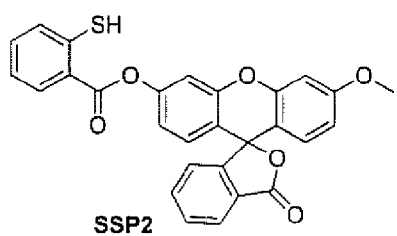
FIGURE 7

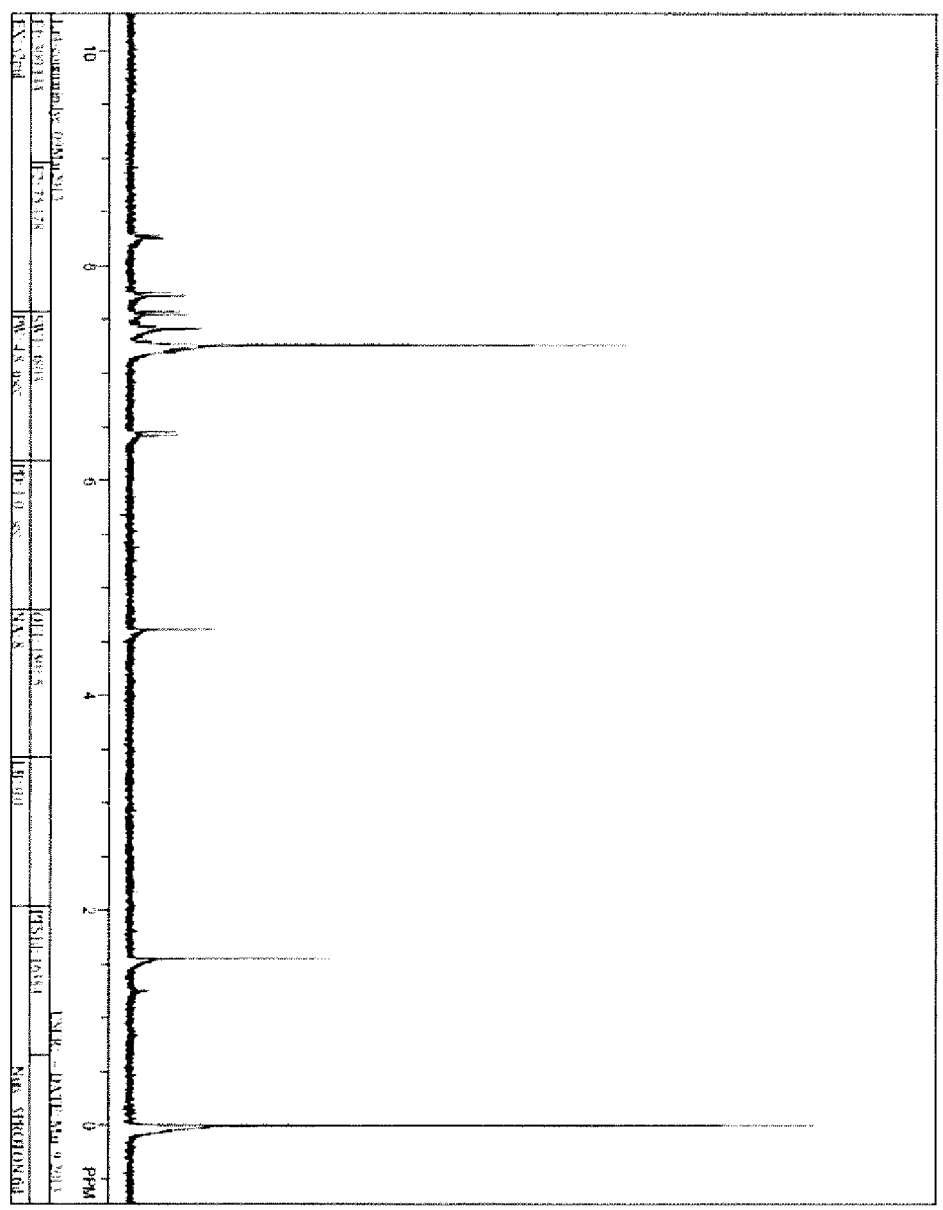
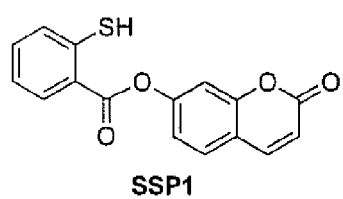
SSP1
FIGURE 8

REACTION-BASED FLUORESCENT PROBES FOR SULFANE SULFUR AND THE APPLICATION IN BIOIMAGING

CROSS-REFERENCE TO RELATED APPLICATIONS

This application claims priority under 35 U.S.C 119 (e) to U.S. Provisional Patent Application No. 61/811,913 filed on 15 Apr. 2013, the complete contents thereof being herein incorporated by reference.

STATEMENT OF GOVERNMENT SUPPORT

This invention was made with government support under R01 GM088226 awarded by the National Institutes of Health. The government has certain rights in the invention.

BACKGROUND OF THE INVENTION

Reactive sulfur species (RSS) are a family of sulfur-containing molecules found in biological systems. These molecules include thiols, S-modified cysteine adducts such as S-nitrosothiols and sulfenic acids, hydrogen sulfide, persulfide, polysulfide, as well as inorganic sulfur derivatives. RSS have attracted increasing attention in biomedical research because these molecules show a variety of physiological functions (M. C. H. Gruhlke and A. J. Slusarenko, *Plant Physiol. Biochem.*, 2012, 59, 98).

For example, hydrogen sulfide ($H_2S$) has been recently recognized as a new gaseous transmitter. The production of endogenous and exogenous administration of $H_2S$ have been demonstrated to exert protective effects in many pathologies (L. Li, P. Rose and P. K. Moore, *Annu. Rev. Pharmacol. Toxicol.*, 2011, 51, 169). Sulfane sulfur compounds are another type of important RSS (E. G. Mueller, *Nat. Chem. Biol.*, 2006, 2, 185). Sulfane sulfur refers to sulfur atom with six valence electrons but no charge (represented as $S^0$). Biologically important sulfane sulfur compounds include persulfides (R—S—SH), hydrogen persulfide ($H_2S_2$), polysulfides (R—S—$S_n$—S—R), and protein-bound elemental sulfur ($S_8$). Sulfane sulfur has unique reactivity to attach reversibly to other sulfur atoms and exhibit regulatory effects in diverse biological systems. These functions include post-transcriptional modification of transfer RNA, synthesis of sulfur-containing cofactors and vitamins, activation or inhibition of enzymes. $H_2S$ and sulfane sulfur always coexist and recent work suggests that sulfane sulfur species, derived from $H_2S$, may be the actual signaling molecules (J. I. Toohey, *Anal. Biochem.* 2011, 413, 1).

Despite the rising interest in sulfane sulfur research, many fundamental questions regarding their production and mechanism of actions remain to be clarified. It is important, therefore, to understand the chemistry and properties of sulfane sulfur species. Accurate and reliable measurement of sulfane sulfur concentrations in biological samples is needed and can provide useful information to understand their functions. Currently the only method for sulfane sulfur detection is based on the reaction with cyanide ion to form thiocyanate, which can then be measured as ferric thiocyanate (J. L. Wood, *Methods Enzymol.*, 1987, 143, 25). However, this method requires post-mortem processing and destruction of tissues or cell lysates. Therefore it cannot be applied in real-time detection in biological samples. Fluorescence assays could be very useful in this field due to the high sensitivity and convenience. Although much progress have been made in the development of fluorescent probes for $H_2S$ (Patent application number US 20120329085 A1) and biological thiols ((a) X. Chen, Y. Zhou, X. Peng and J. Yoon, *Chem. Soc. Rev.*, 2010, 39, 2120; (b) J. Lu and H. Ma, *Chin. Sci. Bull.* (*Chin. Ver.*), 2012, 57, 1462; (c) H. Peng, W. Chen, Y. Cheng, L. Hakuna, R. Strongin and B. Wang, *Sensors*, 2012, 12, 15907; (d) Z. Guo, S, Nam, S. Park and J. Yoon, *Chem. Sci.*, 2012, 3, 2760; (e) K. Xu, M. Qiang, W. Gao, R. Su, N. Li, Y. Gao, Y. Xie, F. Kong and B. Tang, *Chem. Sci.*, 2013, 4, 1079) fluorescent probes for sulfane sulfur detection are still unavailable. Here we report a first reaction-based fluorescent turn-on strategy for the detection of sulfane sulfurs.

SUMMARY OF THE INVENTION

The present invention provides fluorescent probes and methods of their use in detecting sulfane sulfur species. In an exemplary embodiment the invention provides reaction-based fluorescent probes for selective imaging of sulfane sulfur species in living cells under mild conditions. In one embodiment, the invention is selective for sulfane sulfur species including per sulfide, polysulfide, and elemental sulfur.

One of the key benefits of the several embodiments of the invention is that they do not proceed with other biologically relevant sulfur species such as cysteine, glutathione (both reduced and oxidized forms), $H_2S$, thiosulfate, sulfite, and sulfate. An aspect of the invention provides for a fluorescent probe for sensing and imaging sulfane sulfur moieties to include, a nucleophile and fluorphore attached to a linker. Using various embodiments of the invention, the concentration of sulfane sulfur can not only be measured by the fluorescence signal, but also be assessed from the analysis of the benzodithiolone product. Additionally, these methods do not require destruction of living tissues and can be used to detect sulfane sulfur species in living cells. Further, it is easy to use and low in toxicity. These above mentioned qualities bestow the explained invention, as having application in but not limited to biochemical and biomedical research and clinical and drug-development assays.

BRIEF DESCRIPTION OF THE DRAWINGS

FIGS. 3A-B Fluorescence emission spectra of the probes (5 μM) with varied concentrations of $Na_2S_2$ (0, 0.5, 1, 3, 5, 10, 15, 20, 25, 40, 50 μM for curves 1-11, respectively). (FIG. 3A) SSP1, $\lambda_{ex}$=380 nm. (FIG. 3B) SSP2, $\lambda_{ex}$=482 nm. The reactions were carried out for 10 min at rt in PBS buffer (50 mM, pH 7.4) with 1 mM CTAB.

FIGS. 4A-B The plot of fluorescence intensity change of (FIG. 4A) 5.0 μM SSP1 and (FIG. 4B) 5.0 μM SSP2 against varied concentration of $Na_2S_2$ from 0.5 to 25 μM. The reactions were carried out for 10 min at 25° C. in 50 mM PBS buffer with 1 mM CTAB. Data (FIG. 4A) were acquired at 458 nm and excited at 380 nm. Data (FIG. 4B) were acquired at 518 nm and excited at 482 nm.

(FIG. 5A) data of SSP1 (Ex/Em=380/458 nm). (FIG. 5B) data of SSP2 (Ex/Em=482/518 nm). The reactions were carried out for 10 min at rt in PBS buffer (50 mM, pH 7.4) with 1 mM CTAB. (1) probe alone; (2) 1 mM Cys; (3) 1 mM GSH; (4) 1 mM Hcy; (5) 100 μM GSSG; (6) 100 μM $Na_2S$; (7) 100 μM $Na_2S_2O_3$; (8) 100 μM $Na_2SO_3$; (9) 100 μM $Na_2SO_4$; (10) 25 μM $Na_2S_2$; (11) 25 μM Cys-polysulfide; (12) 25 μM $S_8$.

FIGS. 6A-F Fluorescence images of $H_2S_2$ detection in H9c2 cells (a, b, c) and HeLa cells (d, e, f). Cells on glass coverslips were incubated with SSP2 (50 μM) for 20 min, then washed and subjected to different treatments. (a & d) controls (no $Na_2S_2$ was added); (b & e) treated with 50 μM $Na_2S_2$; (c & f) treated with 100 μM $Na_2S_2$.

FIG. 7 $^1$H NMR of SSP2 compound. SSP2 was dissolve in $CD_3Cl$ and the experiment was conducted at 300 MHz FIG. 8 $^1$H NMR of SSP1 compound. SSP1 was dissolve in CD3Cl and the experiment was conducted at 300 MHz FIG. 9 Schematic diagram representing idea of the reaction-based fluorescent probes for sulfane sulfur detection.

DESCRIPTION OF THE INVENTION

Definitions

Figure 1A:
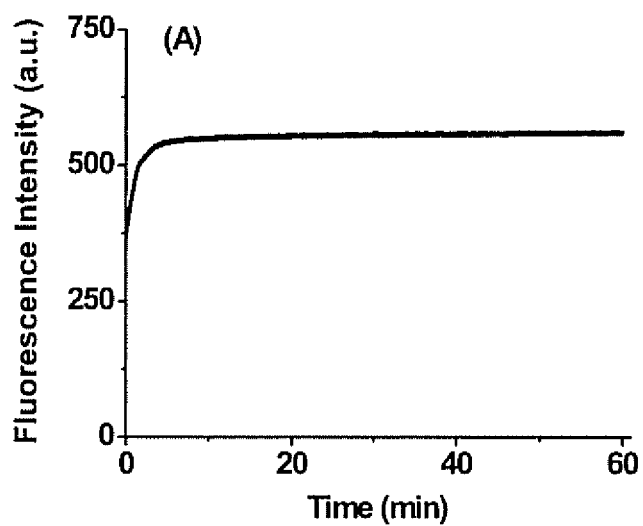
FIGS. 1A-B Time-dependent responses of the probes (5.0 µM) to $Na_2S_2$ (25 µM) in 50 mM PBS buffer (pH 7.4) with 1 mM CTAB at rt. Data were acquired at 458 nm and excited at 380 nm for SSP1 (FIG. 1A); and at 518 nm and excited at 482 nm for SSP2 (FIG. 1B).

The term "nucleophile", by itself means a chemical species that donates an electron-pair to an electrophile to form a chemical bond in a reaction. Because nucleophiles donate electrons, they are by definition Lewis bases. All molecules or ions with a free pair of electrons can act as nucleophiles. Nucleophilic reactions include those in which the nucleophile is an alcohol (alcoholysis), or contains and amino group (aminolysis), etc. Exemplary nucleophiles that may be used in the practice of the invention include but are not limited to: $H_2O$, alcohols, thioacids, thiols, phosphates, halides, isonitriles etc.

The term "Fluorophore", by itself means a chemical compounds containing at least one aromatic groups, or planar or cyclic molecules with several π bonds and can re-emit light upon light excitation.

The term "alkyl", by itself or as part of another substituent, means a straight or branched chain hydrocarbon radical, which may be fully saturated, mono-saturated or polyunsaturated. For convenience, the term alkyl may refer to divalent (i.e., alkalyne) and other multivalent radicals in addition to monovalent radicals. Examples of saturated hydrocarbon radicals include groups such as methyl, ethyl, n-propyl, iso-propyl, n-butyl t-butyl, isobutyl sec-butyl, cyclohexyl, (cyclohexyl) methyl, cyclopropylmethyl, homologs and isomers of, for example, n-pentyl, n-hexyl, n-heptyl, n-octyl and the like. An unsaturated alkyl group is one having one or more double bonds or triple bonds (i.e., alkenyl and alkynyl moieties). Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

Typically, an alkyl (or alkylene) group will have from 1 to 30 carbon atoms. That is, in some embodiments, alkyl refers to an alkyl having a number of carbons selected from $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$ and any combination thereof. In some embodiments, alkyl refers to $C_1$-$C_{25}$ alkyl. In some embodiments, alkyl refers to $C_1$-$C_{20}$ alkyl. In some embodiments, alkyl refers to $C_1$-$C_{15}$ alkyl. In some embodiments, alkyl refers to $C_1$-$C_{10}$ alkyl. In some embodiments, alkyl refers to $C_1$-$C_6$ alkyl.

The term "heteroaryl" refers to aryl containing 1, 2, 3 or 4 heteroatoms selected from N, O and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl.

The term "aryl" refers to a polyunsaturated, aromatic hydrocarbon that can be a single ring or multiple rings (preferably 1, 2 or 3 rings) that are fused together or linked covalently. For convenience, the term aryl may refer to divalent (i.e., arylene) and other multivalent radicals in addition to monovalent radicals. In some embodiments, aryl is a 3, 4, 5, 6, 7 or 8 membered ring that is optionally fused to one or two other 3, 4, 5, 6, 7 or 8 membered rings.

Substituents for alkyl, heteroalkyl, are generically referred to as "alkyl group substituents". In some embodiments, an alkyl group substituent is selected from —R', —OR'. =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R"

Substituents for aryl and heteroaryl groups are generically referred to as "aryl group substituents". In some embodiments, an aryl group substituent is selected from —R', —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN, —NO$_2$ and —N$_3$. In some embodiments. R', R", R"' and R"" are each independently selected from hydrogen, substituted or unsubstituted alkyl, substituted or unsubstituted heteroalkyl.

The symbol ⁓ displayed perpendicular to a bond, or the symbol *, displayed at the end of a bond, indicates the point at which the displayed moiety is attached to the remainder of the molecule.

In some embodiments, the definition of terms used herein is according to IUPAC.

Figure 9:
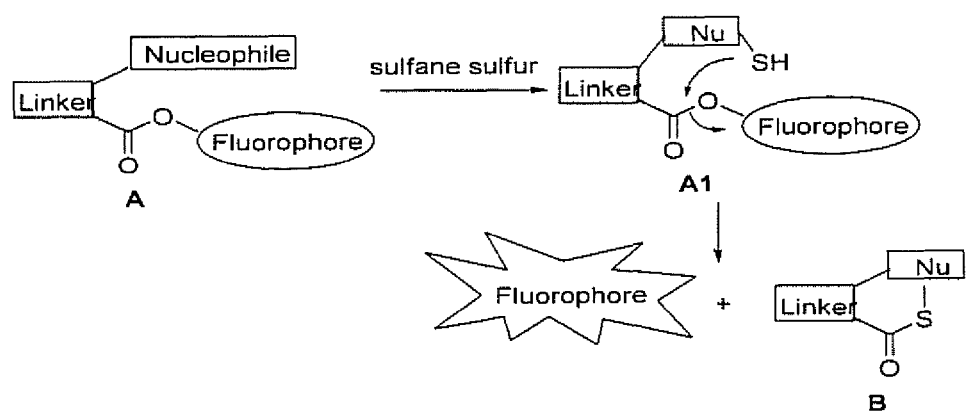

General usefulness of embodiments of our invention lies in the selective detection of sulfane sulfur species in living cells using fluorescence microscopy. Sulfane sulfur compounds are reactive and labile. They commonly exist in the form of thiosulfoxide tautomer. This property provides highly reactive intermediates from which the sulfur atom can be readily removed by nucleophilic groups. In the present invention this reactive property of the sulfane sulfur species is used to design a reaction based fluorescent probes for sulfane sulfurs. As shown in FIG. 9 a probe (A) is designed with a linker attached with a nucleophile and pseudo fluorescent group (e.g. the ester as shown in A), which act as a potential electrophile. This electrophile is positioned suitably for cyclization reaction, so that the sulfane sulfur species can react with the nucleophile of the fluorophore probe and form an SH containing intermediate ($A_t$), which can undergo a spontaneous cyclization reaction to release the fluorophore and product B. This strategy allows to visualize sulfane sulfur related signal via convenient, sensitive, and non-destructive fluorescence measurement. Substrate A does not react with other reactive sulfur species such as $H_2S$, cysteine, glutathione, etc., and therefore, the fluorescent signal is selective only for sulfane sulfurs.

Utilizing the above mentioned concept two exemplary probes SSP1 and SSP2 (Scheme 1) are designed. The fluorescence property of these probes are tested in aqueous PBS buffer solution (pH 7.4). The SH group is used as nucleophile to trap the reactive sulfur atoms in sulfane sulfurs. The resulting intermediates, i.e. —S—SH adducts, undergo a fast intramolecular cyclization to release strong fluorescent molecules (7-hydroxylcoumarin and fluorescein), as well as benzodithiolone 1.

Figure 1B:
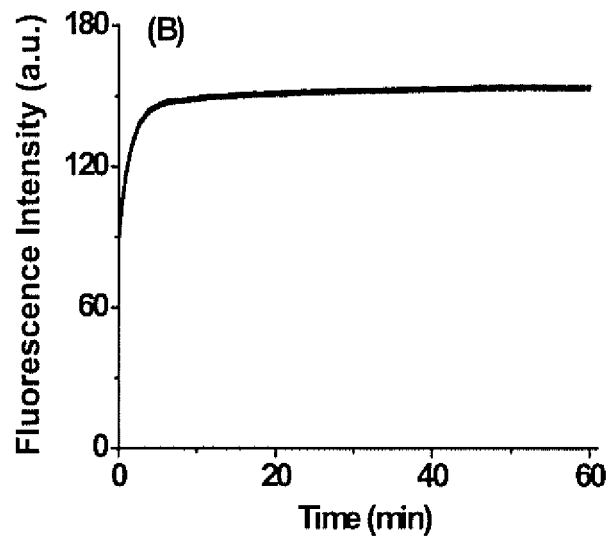
Figure 2A:
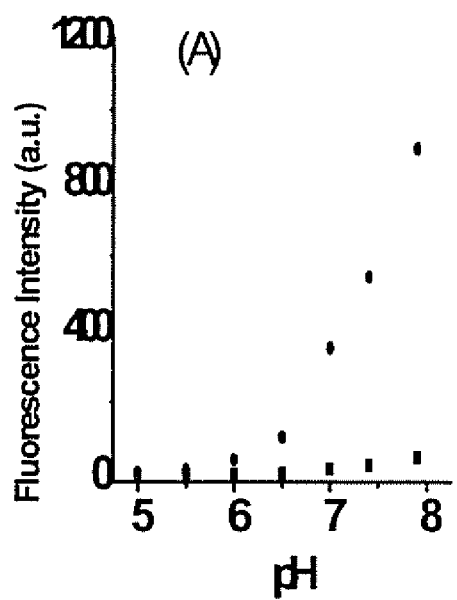
FIGS. 2A-B Fluorescence intensity changes of (FIG. 2A) 5.0 µM SSP1 and (FIG. 2B) 5.0 µM SSP2 at different pH values in the absence (■) or presence (●) of $Na_2S_2$ (25 µM). The reactions were carried out for 10 min at 25° C. in 50 mM PBS buffer with 1 mM CTAB. Data (A) were acquired at 458 nm and excited at 380 nm. Data (B) were acquired at 518 nm and excited at 482 nm.
Figure 2B:
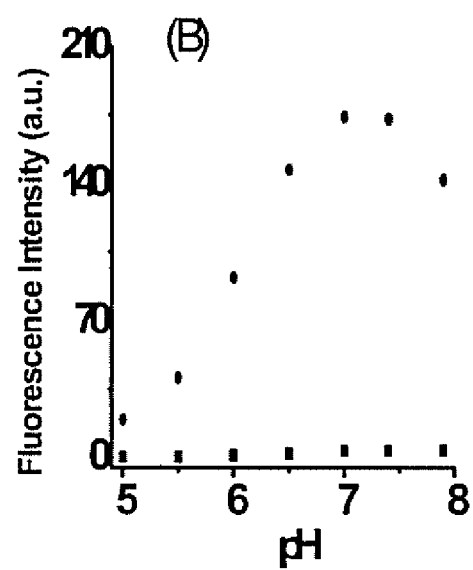

FIGS. 1A-B, the fluorescence intensity of both probes increases dramatically (25 folds for SSP1 and 50 folds for SSP2) if $H_2S_2$ is presented in the solution. In addition, the maximum intensity has been achieved in 5 min, which suggested the fluorescence turn-on reaction is fast. Study of the effects of pH shows that both probes work effectively under neutral to weak basic pHs (7~8) (FIGS. 2A-B). However above pH 8, SSP1 undergoes small amount of hydrolysis, while SSP2 remains stable up to pH 9.

To demonstrate the efficiency of the probes in determining sulfane sulfur concentration, varying concentrations of $Na_2S_2$ (0~50 μM) are tested with SSP1 or SSP2 (5 μM). The fluorescence intensity increased linearly with the concentrations of $Na_2S_2$ changed up to 25 μM, and, thereafter, reached a steady state (FIGS. 3A-B). The detection limits were found to be 73 nM (for SSP1) and 32 nM (for SSP2) demonstrating the probes are highly sensitive and suitable for detecting sulfane sulfurs in living systems (FIGS. 4A-B FIG. 4).

Figure 5A:
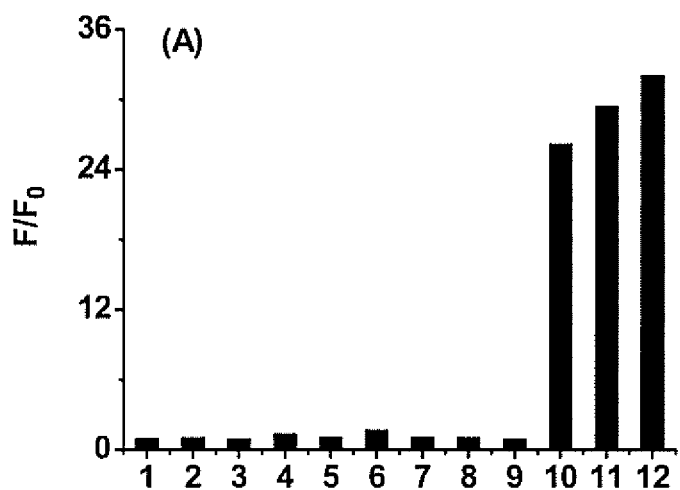
FIGS. 5A-B Fluorescence enhancement ($F/F_0$) of 5.0 μM probes in the presence of various reactive sulfur species.
Figure 5B:
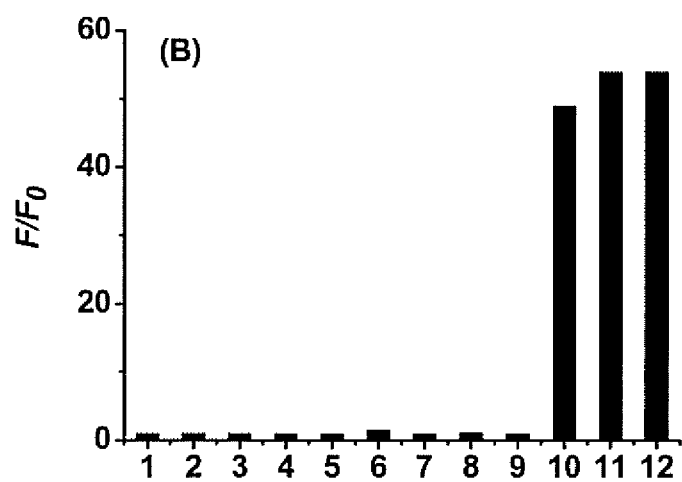

The selectivity of the probes for sulfane sulfurs over other reactive sulfur species (FIGS. 5A-B) have been examined using three representative sulfane sulfur compounds, i.e. $H_2S_2$, cysteine polysulfide (we used a 1:1 mixture of cysteine-trisulfide and tetrasulfide), and elemental sulfur ($S_8$). All these sulfane sulfurs (at 25 μM) show excellent fluorescence responses towards the probes (26~33 folds for SSP1 and 50~60 folds for SSP2). In contrast, other biologically relevant sulfur species, including cysteine (Cys), glutathione (GSH), homocysteine (Hcy), oxidized glutathione (GSSG), $H_2S$ (using $Na_2S$ as the equivalent), thiosulfate, sulfite, and sulfate, show no significant fluorescence enhancement even under much higher concentrations (up to mM levels). In

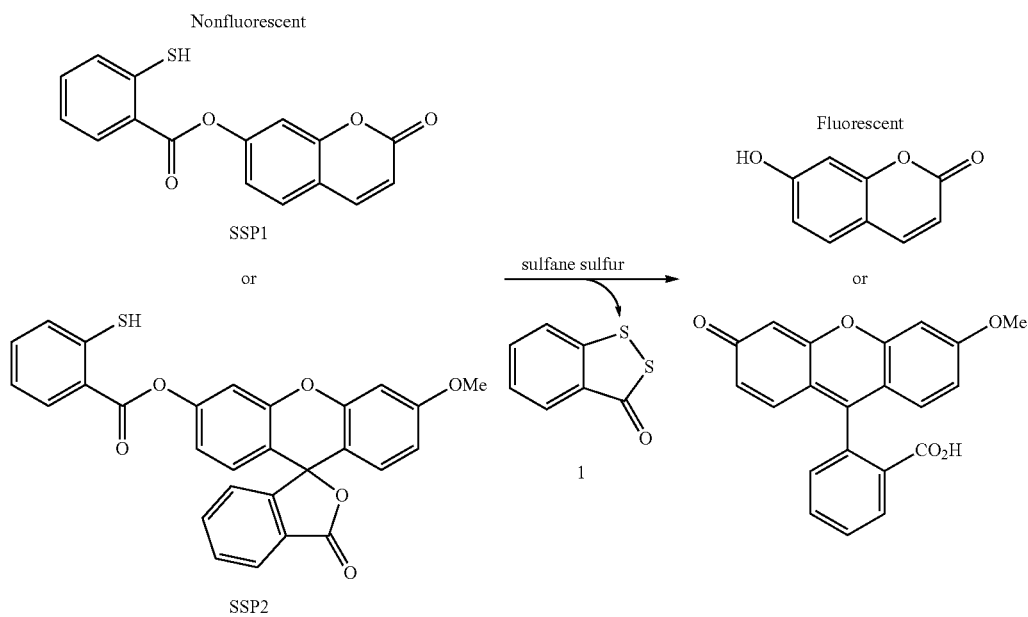

Scheme 1.

Both compounds show low fluorescence quantum yields (Φ=0.06 for SSP1; Φ=0.05 for SSP2) and exhibit no absorption features in the visible region. These compounds are quite stable as no considerable change in fluorescence spectrum is observed after they are stored at 4° C. for two weeks. Fluorescence responses of these probes to a model sulfane sulfur compound hydrogen persulfide ($H_2S_2$), using $Na_2S_2$ as the equivalent have been investigated. As shown in addition, aldehyde species, which are potential electrophiles, show no responses at biologically relevant concentrations. These results demonstrate good selectivity of the probes for sulfane sulfurs. Since persulfide, polysulfide, and elemental sulfur show good reactivity toward the probes, a model reaction to explore the fluorescence turn-on mechanism (Scheme 2) has been conducted. As such, probe model compound 2 has been treated separately with persulfide, polysulfide, and $S_8$ in a 1:1 $CH_3CN$ and PBS buffer mixtures. As expected, benzodithiolone 1 and phenol are isolated with good yields in all three reactions.

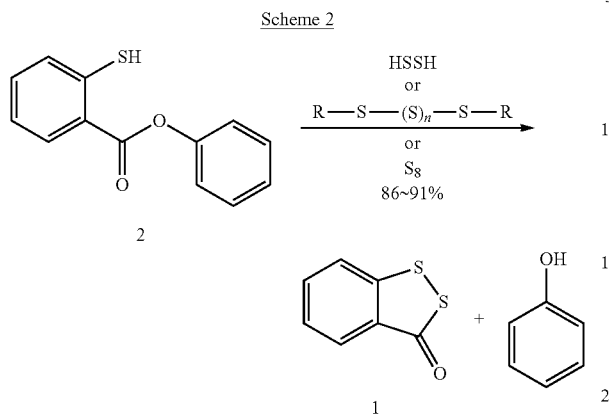

The specificity of the probes for sulfane sulfurs in the presence of other RSS or aldehydes (i.e. interference experiments) have been investigated. It is observed that probes can give significant fluorescence enhancement for sulfane sulfurs even in the presence of other sulfur species or aldehydes. These results demonstrate the probes can be used for monitoring sulfane sulfur in complicated biological systems.

The use of the probes in imaging sulfane sulfurs in cells are tested. Both H9c2 and HeLa cells were used in this study. Briefly, cells are incubated with compound SSP2 for 20 min and then washed with PBS buffer. No significant fluorescent cells was observed (FIG. 6. a-d). However, strong fluorescence in the cells was observed after treatment with $Na_2S_2$ for 30 min. Cells treated with 100 μM $Na_2S_2$ showed obviously stronger fluorescence than cells treated with 50 μM $Na_2S_2$. Therefore, the results demonstrated the probes described in this invention can be used for the detection of sulfane sulfurs in cultured cells.

However, it is to be appreciated that while above description provides for preferred chemical structure probes it is not limited to such an arrangement. As, other chemical structures are equally applicable as disclose herein.

In one aspect, the invention provides a compound having the structure

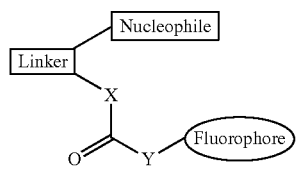

Wherein X is selected from the group containing C, O, N and Y is selected from the group containing O, NH.
Wherein linker is a member selected from:

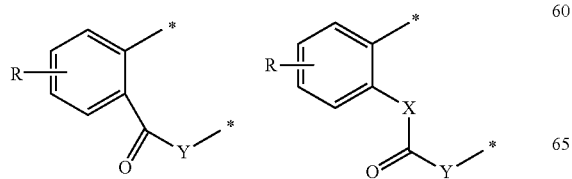

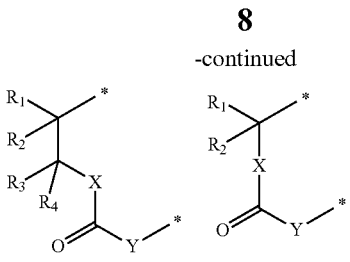

wherein R, $R_1$, $R_2$, $R_3$ and $R_4$ are independently selected from H, substituted or unsubstituted alkyl, substituted or unsubstituted aryl, substituted or unsubstituted heteroalkyl, and substituted or unsubstituted heteroaryl.

Wherein the nucleophile is selected independently from —SH, —SeH, —OH, —$SO_2H$, —$N^+\equiv C^-$, —$CH_2CN$, and —$CH(CN)CO_2R_c$, wherein $R_c$ is substituted or unsubstituted alkyl, substituted or unsubstituted aryl group. wherein the fluorophore is selected from the compound with chemical formula

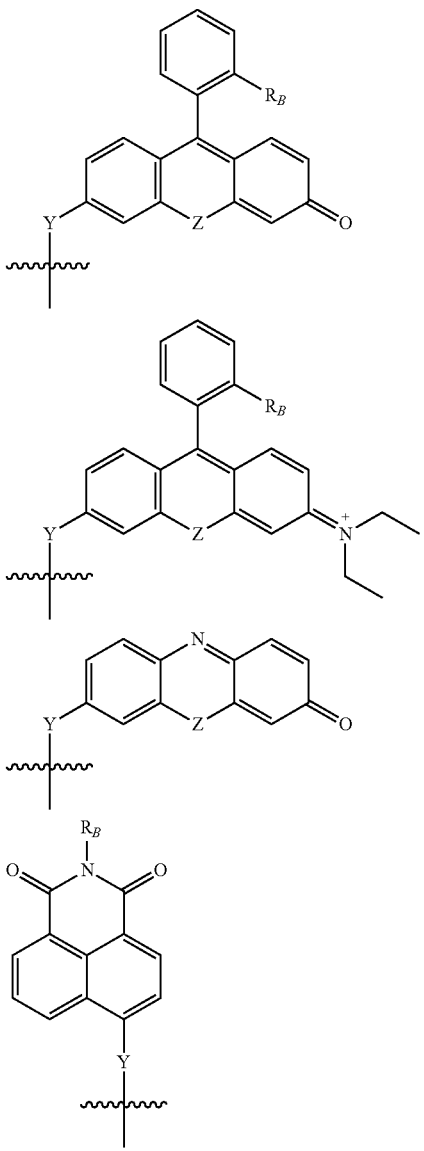

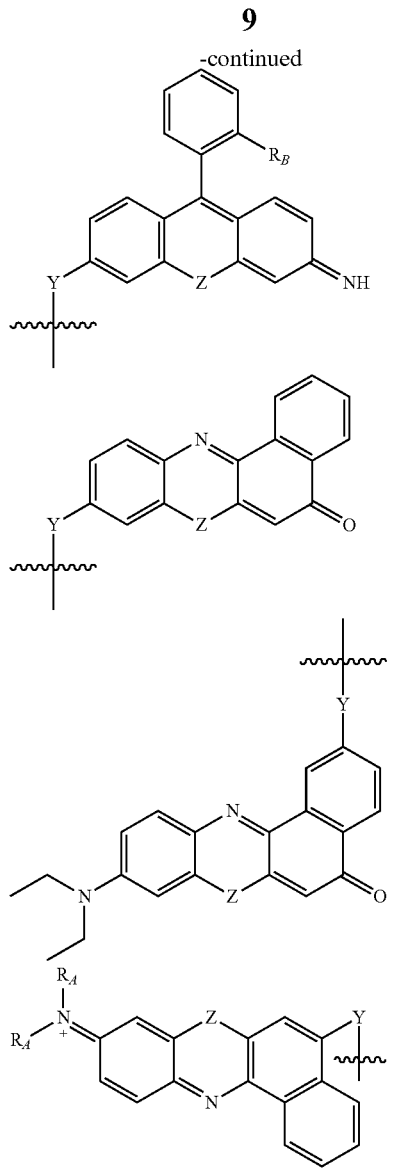

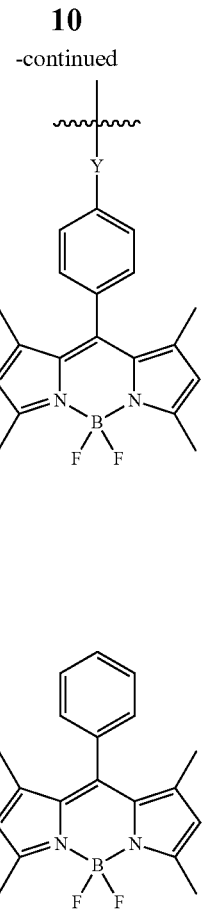

wherein $R_B$ is selected from —COOH, —$(CH_2)_nCH_3$ (n≥0), —$(CH_2)_n$COOH (n≥1), —$(CH_2)_n$COOCH$_3$ (n≥1), or —$(CH_2)_n$COOC$_2$H$_5$ (n≥1); $(CH_2)_n$CONH$(CH_2)_n$PPh$_3$ (n≥1) or —CH$_3$; $R_A$ is —$(CH_2)_nCH_3$ (n≥0), —$(CH_2)_n$COOCH$_3$ or $(CH_2)_n$COOC$_2$H$_5$ (n≥1) and Y is O or NH and Z is O or Si.

In another aspect, the invention provides a fluorophore having a structure selected from wherein Y is O or NH In another aspect, the invention provides a fluorophore having a structure selected from

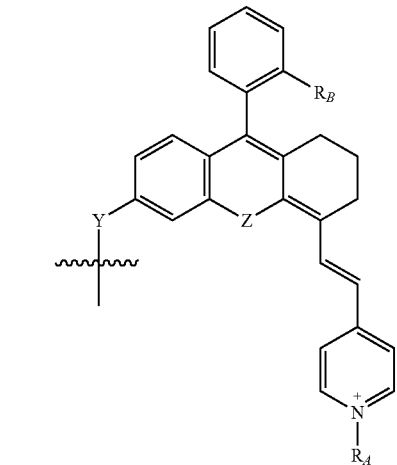

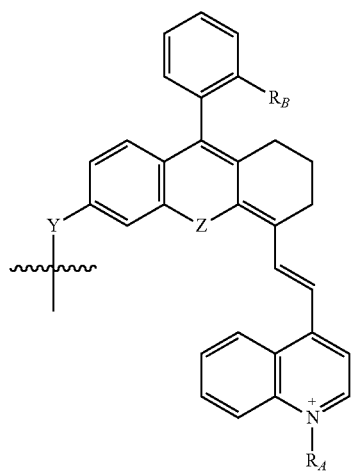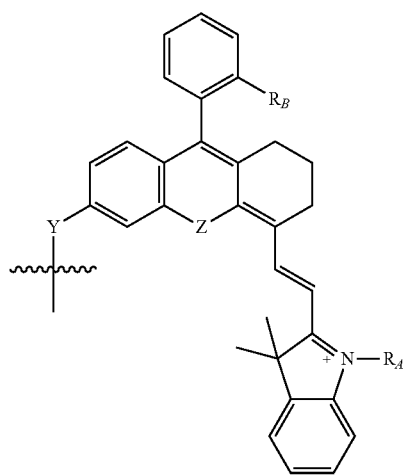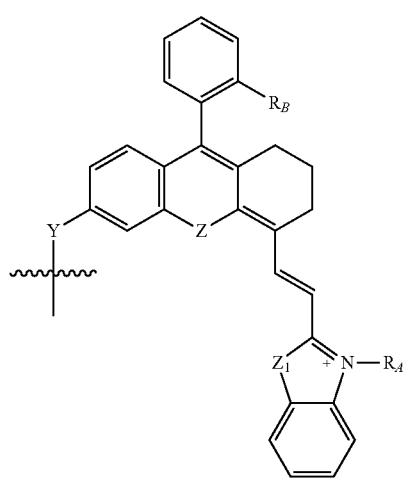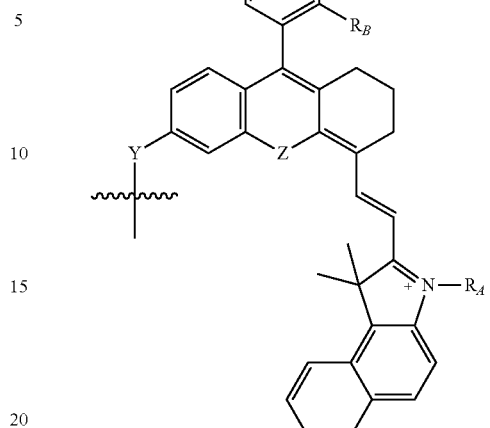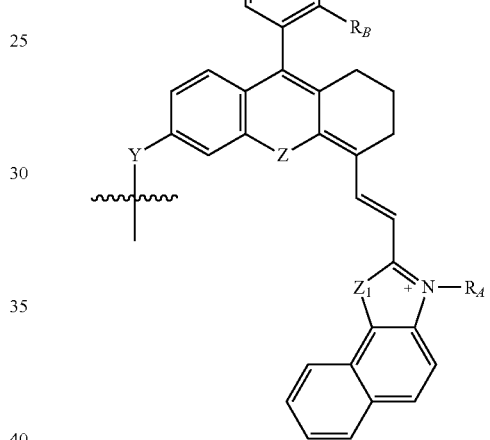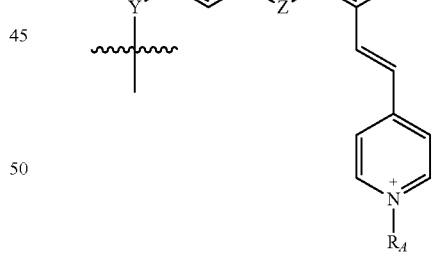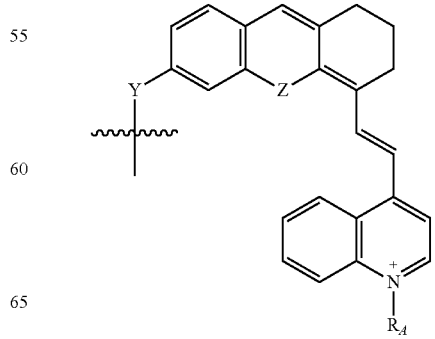

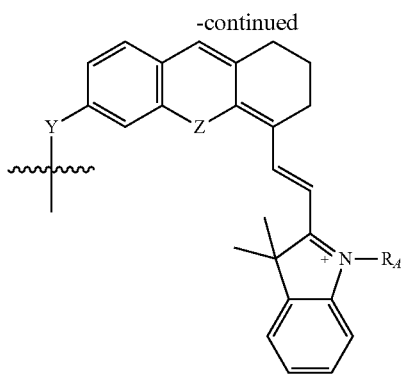

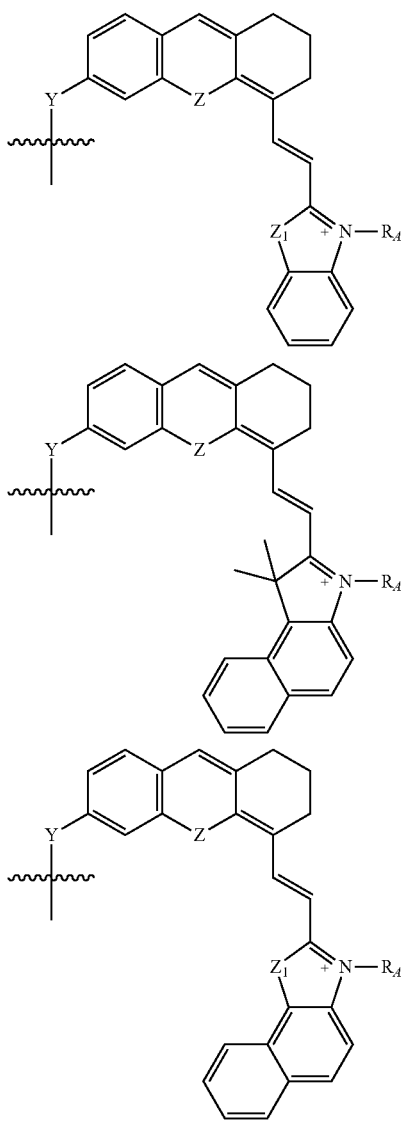

wherein $R_B$ is —COOH or —CH$_3$; Z is selected from O or Si; $Z_1$ is selected from O or S; $R_A$ is selected from (CH$_2$)$_n$CH$_3$ (n≥0)

In another aspect, the invention provides a fluorophore having a chemical formula

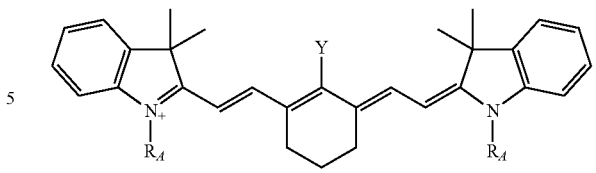

wherein $R_A$ is selected from (CH$_2$)$_n$CH$_3$ (n≥0).

The compounds disclosed herein can be used in real time imaging of sulfane sulfur species in living cells. These probes can be used in various biochemical and biomedical research, enabling study of the role of endogenously produced sulfane sulfur in living cellular model of health and disease. Additionally this probe can be used in clinical and drug-development assay by providing rapid method to assess the level of sulfane sulfur.

In another aspect, the invention provides a method of detecting a sulfane sulfur species in a sample comprising: a) contacting the sample with a probe disclosed herein; b) detecting the reaction product emitting a detectable signal.

In some embodiments, the sulfane sulfur species is persulfide.

In some embodiments, the sample comprises a cell.

In some embodiments, the cell is living cell.

EXAMPLES

SSP1 and SSP2

Materials and Methods:

All solvents were reagent grade. Reactions were magnetically stirred and monitored by thin layer chromatography (TLC) with 0.25 mm pre-coated silica gel plates. Flash chromatography was performed with silica gel 60 (particle size 0.040-0.062 mm). Yields refer to chromatographically and spectroscopically pure compounds, unless otherwise stated. Proton and carbon-13 NMR spectra were recorded on a 300 MHz spectrometer.

Chemical Synthesis

Chemical shifts are reported relative to chloroform (δ 7.26) for $^1$H NMR and chloroform (δ 77.0) for $^{13}$C NMR. Absorption spectra were recorded on a Lambda 20 UV/VIS spectrophotometer using 1 cm quartz cells. Fluorescence excitation and emission spectra were measured on Cary Eclipse fluorescence spectrophotometer.

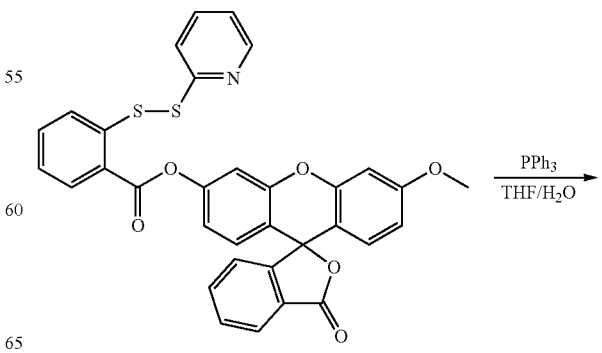

S1

-continued

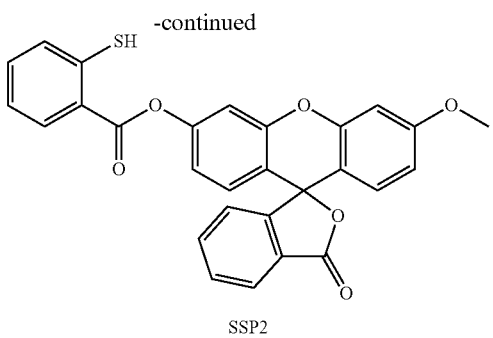

SSP2

Probe SSP2: to a solution of compound S1[1] (110.0 mg, 0.186 mmol) in THF/H$_2$O (6.0 mL/3.0 mL) was added PPh$_3$ (121.9 mg, 0.47 mmol) slowly at 0° C. The mixture was allowed to warm to room temperature (r.t.) and stirred for 0.5 hours (h). Tetrahydrofuran (THF) was removed under reduced pressure and 10 mL of HCl (1N) was added to acidify the solution. Then the mixture was extracted with CH$_2$Cl$_2$ (20 mL). The organic layer was separated and washed with brine. After dried by MgSO$_4$, the solvent was removed under reduced pressure and the resulted residue was purified by flash column chromatography. SSP2 was obtained as a white solid (72.6 mg, 81% yield). $^1$H NMR (FIG. 7) (300 MHz, CD$_3$Cl) δ 3.89 (s, 3H), 4.62 (s, 1H), 6.61-6.91 (m, 5H), 7.40-7.71 (m, 5H), 7.66 (m, 2H), 8.03 (dd, J=6.3, 0.9 Hz, 1H), 8.24 (d, J=7.8 Hz, 1H); $^{13}$C NMR (75 MHz, CD$_3$Cl) δ 169.6, 164.9, 161.7, 153.3, 152.5, 152.2, 152.0, 140.0, 135.5, 133.7, 132.5, 131.4, 130.1, 129.4, 129.3, 126.7, 125.3, 125.2, 124.7, 124.3, 117.8, 117.2, 112.2, 111.1, 110.8, 101.1, 82.7, 55.8; MS (ESI$^+$) m/z 505.0 (M+Na$^+$); IR 3063, 2945, 2551, 1761, 1610, 1496, 1462, 1418. mp 115-116° C.

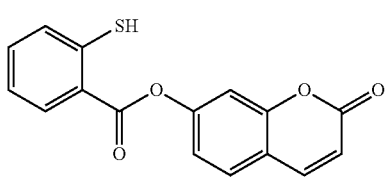

SSP1

Probe SSP1 was prepared using the same method as for SSP2. $^1$H NMR (FIG. 8) (300 MHz, CD$_3$Cl) δ 4.61 (s, 1H), 6.44 (d, J=9.6 Hz, 1H), 7.17-7.28 (m, 3H), 7.41 (m, 2H), 7.56 (d, J=8.4 Hz, 1H), 7.73 (d, J=9.6 Hz, 1H), 8.26 (d, J=8.4 Hz, 1H). $^{13}$C NMR (75 MHz, CD$_3$Cl) δ 164.4, 160.2, 154.6, 153.0, 142.8, 139.9, 133.5, 132.2, 131.2, 128.6, 124.9, 124.2, 118.6, 116.8, 116.1, 110.6; MS (ESI$^+$) m/z 321.0 (M+Na$^+$); IR 3094, 2922, 2530, 1731, 1618, 1583, 1461, 1395. mp 141-142° C.

Example 1.2

Model Reactions of the Probe with Sulfane Sulfur Species

To the solution of 2 (23.0 mg, 0.1 mmol) in CH$_3$CN (2.5 mL) and PBS buffer (2.5 mL, 100 mM, pH 7.4) was added Na$_2$S$_2$ (55 mg, 0.5 mmol).

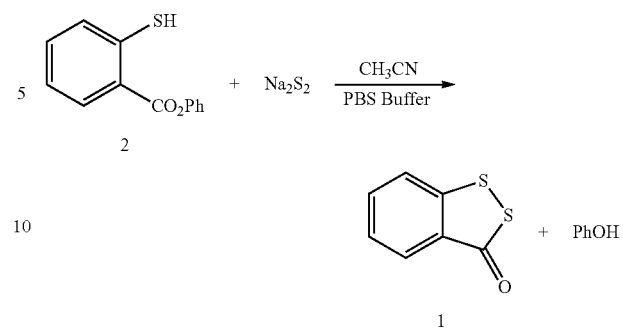

The mixture was stirred for 1 hour at rt and then diluted with CH$_2$Cl$_2$. The organic layer was separated and dried by MgSO$_4$, and concentrated. Purification by flash column chromatography afforded compound 1[2] as light yellow solid (15.2 mg, 91% yield).

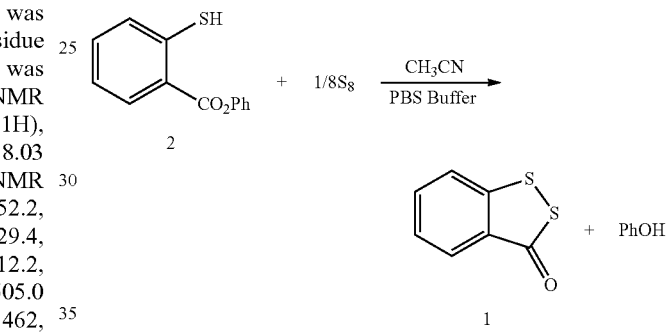

To the solution of 2 (23.0 mg, 0.1 mmol) in CH$_3$CN (2.0 mL), CCl$_4$ (0.5 mL) and PBS buffer (2.5 mL, 100 mM, pH 7.4) was added elemental sulfur (16 mg, 0.5 mmol). The mixture was stirred for 1 hour at rt and then diluted with CH$_2$Cl$_2$. The organic layer was separated and dried by MgSO$_4$, and concentrated. Purification by flash column chromatography afforded compound 1 as light yellow solid (14.8 mg, 88% yield).

To the solution of 2 (23.0 mg, 0.1 mmol) in CH$_3$CN (2.5 mL), and PBS buffer (2.5 mL, 100 mM, pH 7.4) was added S3 (105 mg, 0.5 mmol). The mixture was stirred for 1 hour at rt and then diluted with CH$_2$Cl$_2$. The organic layer was separated and dried by MgSO$_4$.

Example 1.3

Quantum Yields

The quantum yield was calculated according to the equation:[3]

$$(\Phi_{sample} = \Phi_{standard} * (I_{sample}/I_{standard}) * (A_{standard}/A_{sample}) * (n_{sample}/n_{standard})^2)$$

Φ denotes the quantum yield; I denotes the area under the fluorescence band; A denotes the absorbance at the excitation wavelength; n denotes the refractive index of the solvent.

For quantum yield of SSP1, it was determined using 7-hydroxycoumarin as a standard by comparing the area under the corrected emission spectrum of the test sample with that of a solution of 7-hydroxycoumarin excited at 330 nm in sodium phosphate buffer (0.1 M; pH 7.4), which has a quantum efficiency of 0.76 according to the literature.

For quantum yield of SSP2, Quantum yield was determined using fluorescein as a standard by comparing the area under the corrected emission spectrum of the test sample with that of a solution of fluorescein excited at 490 nm in 0.1 N NaOH, which has a quantum efficiency of 0.85 according to the literature.

Example 1.4

Preparation of the Solutions and Fluorescence Measurements

The stock solution of SSP1 (1 mM) and SSP2 (1 mM) were prepared in CH$_3$CN, respectively. The solutions of various testing species were prepared from Cysteine (Cys), GSH, Homocysteine (Hcy), Glutathione disulfide (GSSG), Na$_2$S.9H$_2$O, Na$_2$S$_2$O$_3$, Na$_2$SO$_3$, Na$_2$SO$_4$, Na$_2$S$_2$ in 50 mM PBS buffer. The stock solution of Cetrimonium bromide (CTAB, 100 mM) and S$_8$ (10 mM) were prepared in EtOH, respectively. The stock solution of Cys-polysulfide (10 mM) was prepared in CH$_3$CN. All the test solution need to be freshly prepared.

Unless otherwise noted, all the measurements were carried out for 10 min at 25° C. in 50 mM PBS buffer (pH 7.4) with 1 mM CTAB according to the following procedure. In a test tube, 3.5 mL of 50 mM PBS buffer (pH 7.4) and 40 μL of the stock solution of CTAB were mixed, and then added 20 μL of the stock solution of SSP1 or SSP2. The resulting solution was mixed well, followed by addition of a requisite volume of testing species sample solution. The final volume of the reaction solution was adjusted to 4 mL with 50 mM PBS buffer (pH 7.4). After mixing and then standing for 10 min at room temperature, a 4-mL portion of the reaction solution was transferred into a 1-cm quartz cell to measure fluorescence with $\lambda_{ex}$=380 nm (for SSP1) or 482 nm (SSP2). In the meantime, a blank solution containing no testing species sample was prepared and measured under the same conditions for comparison. All the measurements were repeated three times and data reported were averages.

Example 1.5

Cell Culture and Fluorescence Imaging

H9c2 cells and HeLa cells were grown on glass-bottom culture dishes (Corning Inc.) in DMEM supplemented with 10% (v/v) FBS, penicillin (100 U/mL) and streptomycin (100 μg/mL) at 37° C. under a humidified atmosphere containing 5% CO$_2$. Before use, the adherent cells were washed one time with FBS-free DMEM. For intracellular H$_2$S$_2$ imaging, the cells were incubated with 50 μM SSP2 in FBS-free DMEM (containing 200 μM CTAB) at 37° C. for 20 min. After removal of excess probe and washed with PBS (pH 7.4), the cells were incubated with 50 or 100 uM Na$_2$S$_2$ for 30 min in PBS buffer (pH 7.4, containing 500 μM CTAB). Cell imaging was carried out after washing the cells three times with PBS (pH 7.4).

The invention claimed is:

1. A fluorescent probe comprising:
    a linker;
    a nucleophile;
    a fluorophore;
    said fluorescent probe having the formula

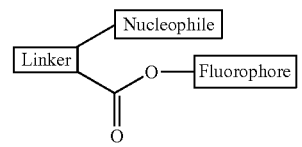

wherein
the fluorophore is

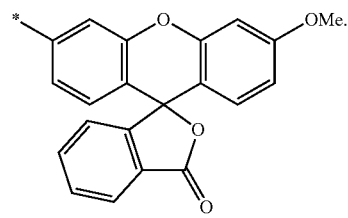 [SMILES: *c1ccc2c(c1)Oc1cc(OC)ccc1C21OC(=O)c2ccccc21]

2. The fluorescent probe of claim 1 wherein the linker is:

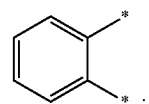

3. The fluorescent probe of claim 1 wherein the nucleophile is selected from the group consisting of —SH, —SeH, —OH, —SO$_2$H, —CH$_2$CN, and —CH(CN)CO$_2$R$_C$, wherein R$_C$ is selected from the group consisting of substituted alkyl, unsubstituted alkyl, substituted aryl and unsubstituted aryl.

4. The fluorescent probe of claim 2 wherein the nucleophile is —SH.

5. The fluorescent probe of claim 1 the wherein the chemical structure of the fluorescent probe is

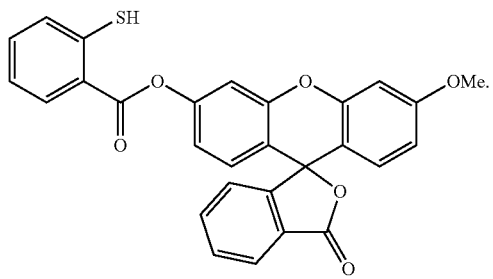 [SMILES: COc1ccc2c(c1)Oc1cc(OC(=O)c3ccccc3S)ccc1C21OC(=O)c2ccccc21]

6. The fluorescent probe of claim 1 wherein said fluorescent probe is non-fluorescent until it reacts with sulfur atoms in sulfane sulfurs, and upon reaction with said sulfur atoms the fluorescent probe releases the fluorophore which provides a fluorescent indication of binding said sulfur atoms.

7. The fluorescent probe of claim 1 wherein said fluorescent probe releases on reacting with said sulfur atoms.

* * * * *